(12) United States Patent
Kowalski et al.

(10) Patent No.: US 6,211,591 B1
(45) Date of Patent: Apr. 3, 2001

(54) LINEAR/ROTARY ELECTROMAGNETIC DEVICE

(75) Inventors: Keith Kowalski, Bethlehem; Albert Palmero, Middlefield, both of CT (US)

(73) Assignee: Tri-Tech, Inc., Waterbury, CT (US)

( * ) Notice: Subject to any disclaimer, the term of this patent is extended or adjusted under 35 U.S.C. 154(b) by 0 days.

(21) Appl. No.: 09/486,664

(22) PCT Filed: Aug. 27, 1998

(86) PCT No.: PCT/US98/17801

§ 371 Date: Feb. 26, 2000

§ 102(e) Date: Feb. 26, 2000

(87) PCT Pub. No.: WO99/10965

PCT Pub. Date: Apr. 3, 1999

Related U.S. Application Data

(60) Provisional application No. 60/057,683, filed on Aug. 27, 1997.

(51) Int. Cl.[7] ............................... H02K 7/06; H02K 7/20
(52) U.S. Cl. ........................... 310/80; 310/112; 318/35
(58) Field of Search ........................... 310/12, 13, 14, 310/20, 15, 17, 80, 112; 318/115, 35; 29/739, 740, 741, 743, 744, 834

(56) References Cited

U.S. PATENT DOCUMENTS 5,093,596 * 3/1992 Hammer ................................ 310/191

5,789,830 * 8/1998 Portegies et al. ...................... 310/12

* cited by examiner

*Primary Examiner*—Nestor Ramirez
*Assistant Examiner*—Judson H. Jones
(74) *Attorney, Agent, or Firm*—John H. Crozier

(57) ABSTRACT

In a preferred embodiment, a linear/rotary electromagnetic device, including: a housing (20); first and second stators (22 and 40) disposed in the housing, first and second rotors (24/26 and 42/44) disposed in the housing and magnetically interacting, respectively, with the first and second stators; the first stator and the first rotor comprising a rotary motor; the second stator and the second rotor comprising an electromagnetic brake; a shaft (28) extending through a portion of the housing and axially through the first and second rotors, the shaft having a threaded portion (50) extending through a complementary threaded portion (44) of one of the first and second rotors; whereby; when the electromagnetic brake is locked and the rotary motor is rotated in a first direction, the shaft will move axially in a first direction; when the electromagnetic brake is locked and the rotary motor is rotated in the second direction, the shaft will move axially in a second direction; and when the electromagnetic brake is released and the rotary motor is rotated, the shaft will rotate with the rotary motor.

10 Claims, 4 Drawing Sheets

US 6,211,591 B1

LINEAR/ROTARY ELECTROMAGNETIC DEVICE

This application is a 371 of PCT/US98/17801 filed Aug. 27, 1998, which claims benefit of Provisional No. 60/057, 683 filed Aug. 27, 1997.

TECHNICAL FIELD

The present invention relates to electromagnetic devices generally and, more particularly, but not by way of limitation, to a novel electromagnetic device which selectively provides rotary and/or linear motion at a single output shaft.

BACKGROUND ART

In certain applications, it is desirable to have a shaft which may selectively rotate and/or reciprocate. Such an application, for example, is in the robotic picking and placing of components where it may be required to axially move a component to an insertion position and then rotate the component to screw it in place. Conventional motor arrangements to accomplish such motion are often complicated and heavy, a substantial disadvantage for robotics applications. Another type of application requiring a shaft which may selectively rotate and/or reciprocate is in the precise control of laparoscopic and other such medical instruments.

In either type of application, it is frequently required that the linear motion be locked while rotary motion takes place. For a rotary/linear motor, this makes it desirable that the linear and rotary motions be controllable independently of one another.

Accordingly, it is a principal object of the present invention to provide an electromagnetic device which selectively provides both linear and/or rotary motion at a single output shaft.

It is an additional object of the invention to provide such an electromagnetic device in which linear and rotary motions are controllable independently of one another.

It is another object of the invention to provide such an electromagnetic device in which linear motion can be locked while rotary motion is provided.

It is a further object of the invention to provide such an electromagnetic device that is simple and economical to manufacture.

An additional object of the invention is to provide such an electromagnetic device that is lightweight and compact.

Other objects of the present invention, as well as particular features, elements, and advantages thereof, will be elucidated in, or be apparent from, the following description and the accompanying drawing figures.

DISCLOSURE OF INVENTION

The present invention achieves the above objects, among others, by providing, in a preferred embodiment, a linear/rotary electromagnetic device, comprising: a housing; first and second stators disposed in said housing; first and second rotors disposed in said housing and magnetically interacting, respectively, with said first and second stators; said first stator and said first rotor comprising a rotary motor; said second stator and said second rotor comprising an electromagnetic brake; a shaft extending through a portion of said housing and axially through said first and second rotors, said shaft having a threaded portion extending through a complementarily threaded portion of one of said first and second rotors; whereby; when said electromagnetic brake is locked and said rotary motor is rotated in a first direction, said shaft will move axially in a first direction; when said electromagnetic brake is locked and said rotary motor is rotated in a second direction; and when said electromagnetic brake is released and said rotary motor is rotated, said shaft will rotate with said rotary motor.

BRIEF DESCRIPTION OF DRAWINGS

Understanding of the present invention and the various aspects thereof will be facilitated by reference to the accompanying drawing figures, submitted for purposes of illustration only and not intended to define the scope of the invention, on which.

BEST MODE OF CARRYING OUT THE INVENTION

Figure 1:
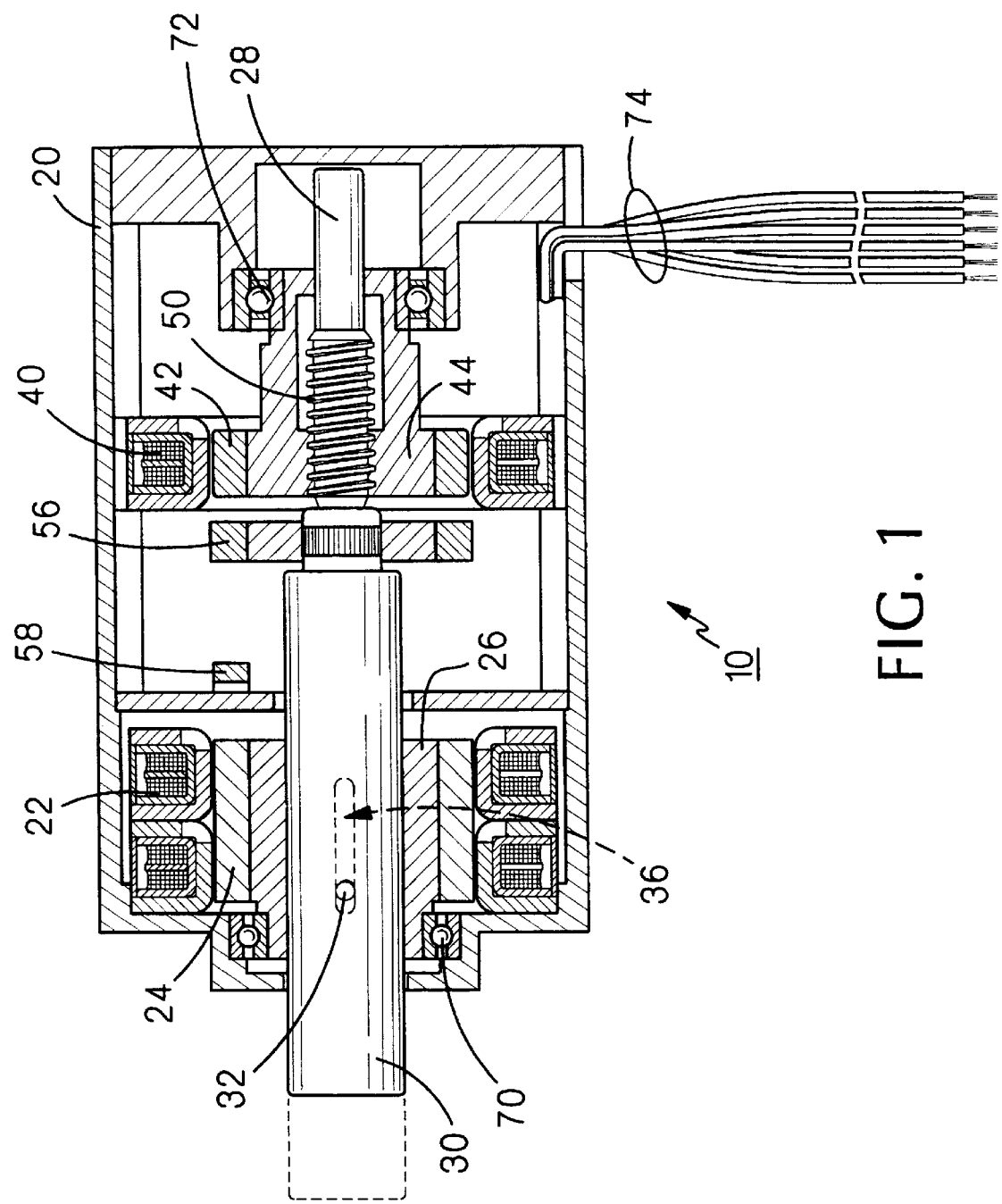
FIG. 1 is a side elevational view, partially in cross-section and partially cut-away, of an electromagnetic device according to a first embodiment of the present invention.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may be seen also on other views.

FIG. 1 illustrates a linear/rotary electric motor, constructed according to a first embodiment of the present invention, the motor being generally indicated by the reference numeral 10. Motor 10 includes a housing 20 having an annular stator structure 22 fixedly mounted therein in magnetic interacting relationship with an annular permanent magnet 24 fixedly mounted on an annular bushing 26, the latter two elements comprising a motor rotor. A shaft 28 extends coaxially through housing 20 and includes a cylindrical portion 30 extending coaxially through bushing 26. Shaft 28 is secured against rotation relative to bushing 26 by means of a pin 32 extending through and fixedly attached to the bushing and extending through cylindrical portion 30. To permit axial movement of shaft 28 relative to bushing 26, pin 32 extends through an axially extending slot 36 defined through bushing 26.

Housing 20 also includes fixedly mounted therein a second annular stator 40 magnetically interacting with an annular permanent magnet 42 fixedly mounted on an annular, internally threaded nut 44, the second stator and the permanent magnet comprising an electromagnetic brake. A threaded portion 50 of shaft 28 extends through nut 44, the threaded portion and the internal threads of nut 44 being complementary. An annular permanent magnet 56 is fixedly mounted on shaft 28 and magnetically interacts with a Hall cell or similar sensor 58 fixedly mounted in housing 20.

In use, initially as rotor 24/26 rotates in one direction and electromagnetic brake 40/42 is locked by means of applying electrical current to stator 40, shaft 28 will move axially to the left on FIG. 1, while rotating, by virtue of the complementarily threaded portions of nut 44 and shaft portion 50. When the maximum extent of linear motion of shaft 28 is reached, magnet 56 triggers Hall cell 58 and brake 40/42 is released. With brake 40/42 released, further motion of shaft 28 is purely rotary. When it is desired to return to the home position shown on FIG. 1, brake 40/42 is locked and rotation of rotor 24/26 in the opposite direction causes shaft 28 to move to the right on FIG. 1 while rotating.

Bearings 70 and 72 provide axial and radial support for shaft 28 and wires 74 are provided for connection between control means (not shown) and the electrical elements of motor 20.

Figure 2:
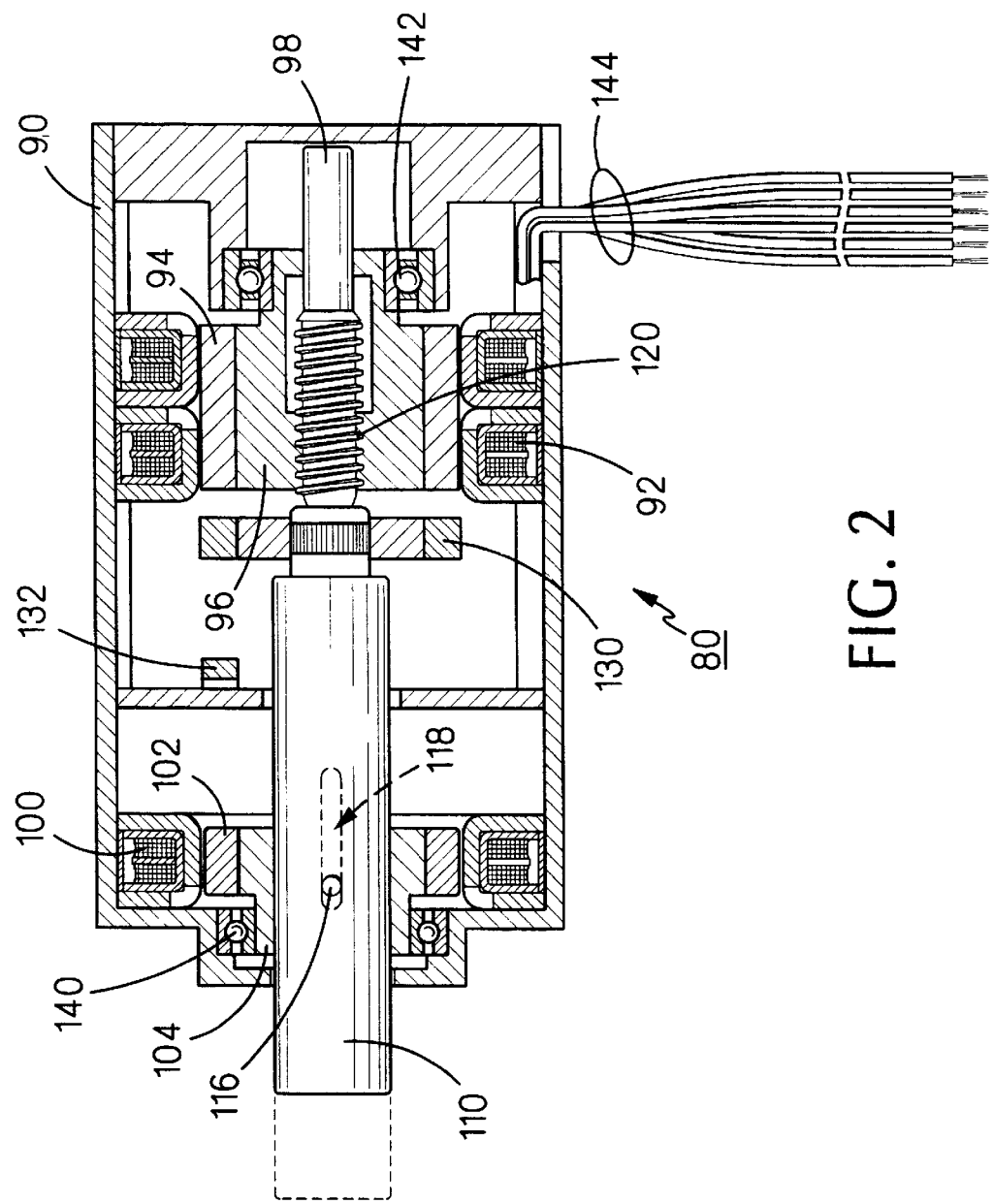
FIG. 2 is a side elevational view, partially in cross-section and partially cut-away, of an electromagnetic device according to a second embodiment of the present invention.

FIG. 2 illustrates a linear/rotary electric motor constructed according to a second embodiment of the present invention, the motor being generally indicated by the reference numeral 80. Motor 80 includes a housing 90 having an annular stator structure 92 fixedly mounted therein in magnetic interacting relationship with an annular permanent magnet 94 fixedly mounted on an annular, internally threaded bushing 96, the latter two elements comprising a motor rotor.

Housing 90 also includes fixedly mounted therein a second annular stator 100 magnetically interacting with an annular permanent magnet 102 fixedly mounted on an annular bushing 104, the second stator and the permanent magnet comprising an electromagnetic brake. A shaft 98 extends coaxially through housing 90 and includes a cylindrical portion 110 extending coaxially through bushing 104. Shaft 98 is secured against rotation relative to bushing 104 by means of a pin 116 extending through the bushing and through and fixedly attached to cylindrical portion 110. To permit axial movement of shaft 98 relative to bushing 104, pin 116 extends through an axially extending slot 118 defined through bushing 104.

A threaded portion 120 of shaft 98 extends through bushing 96, threaded portion 120 and the internal threads of the bushing being complementary. An annular permanent magnet 130 is fixedly mounted on shaft 98 and magnetically interacts with a Hall cell or similar sensor 132.

Bearings 140 and 142 provide axial and radial support for shaft 98 and wires 144 are provided for connection between control means (not shown) and the electrical elements of motor 80.

In use for linear motion, as rotor 94/96 rotates in one direction and electromagnetic brake 100/102 is locked, shaft 98 will move axially to the left on FIG. 2, without rotation of the shaft. When the maximum extent of linear motion of shaft 98 is reached, magnet 130 triggers Hall cell 132, brake 100/102 is released, and the motion of the shaft is purely rotary. Further linear motion of shaft 98 is prevented by virtue of the ends of pin 116 engaging the ends of slot 118. When it is desired to return to the home position shown on FIG. 2, brake 100/102 is locked and rotation of rotor 94/96 in the opposite direction moves shaft 98 to the right on FIG. 2.

Figure 3:
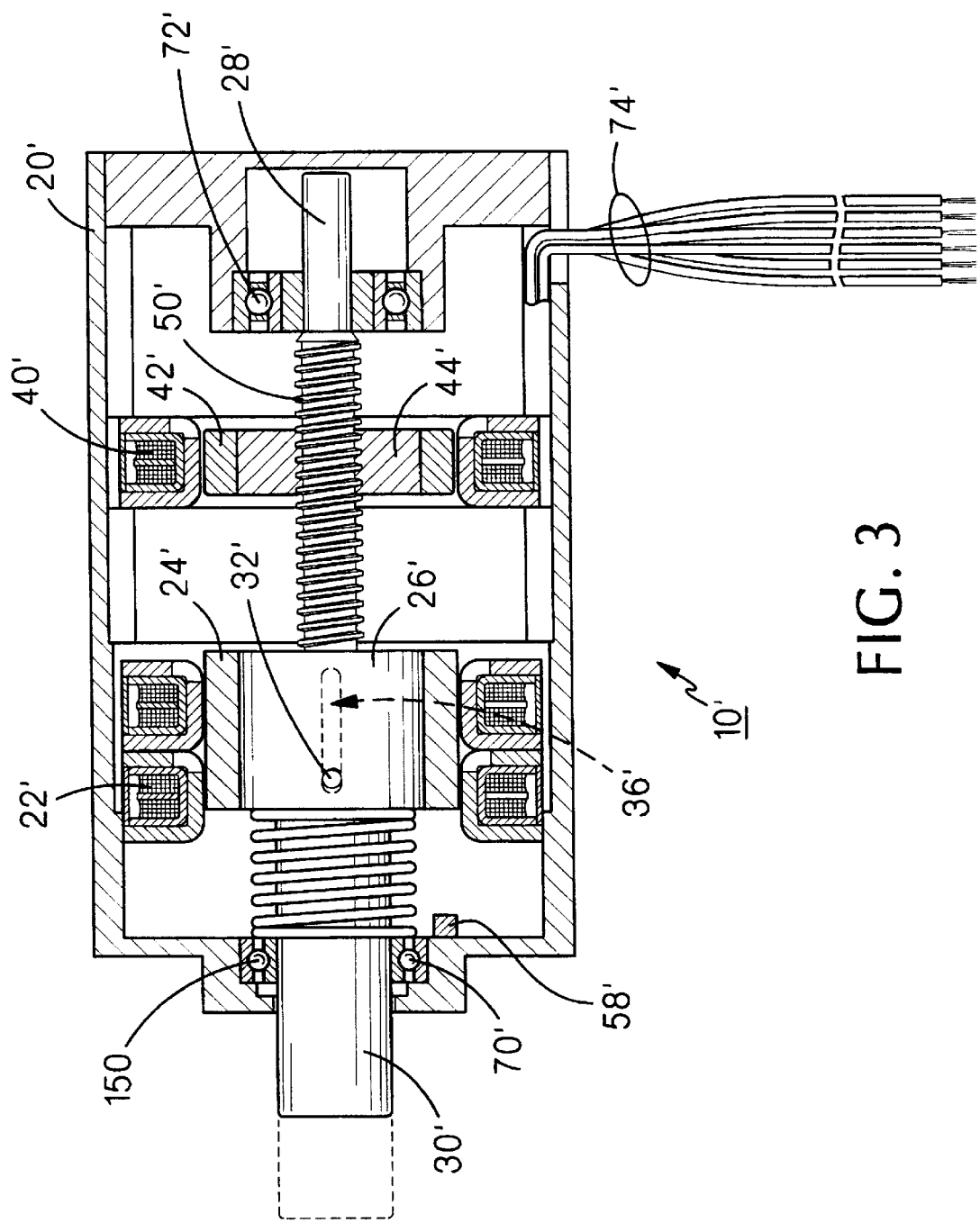
FIG. 3 is a side elevational view, partially in cross-section and partially cut-away, of an electromagnetic device according to a third embodiment of the present invention.

FIG. 3 illustrates a linear/rotary electric motor, constructed according to a third embodiment of the present invention, the motor being generally indicated by the reference numeral 20'. Since motor 20' is a variation of motor 20 (FIG. 1), the common elements thereof are given primed reference numerals and reference should be made to FIG. 1 for a description of the elements and the operation thereof to the extent not described with reference to FIG. 3.

The differences between motor 20 and motor 20' is that, in the latter, permanent magnet 56 (FIG. 1) has been eliminated and Hall cell 58 is triggered when approached by permanent magnet 24' of rotor 24'/26'. Also, motor 20' includes a return spring 150 disposed between bushing 26' and bearing 70' to return shaft 28' to its home position. Return spring 150 may not be required if motor 20' is operating in a vertical position.

Figure 4:
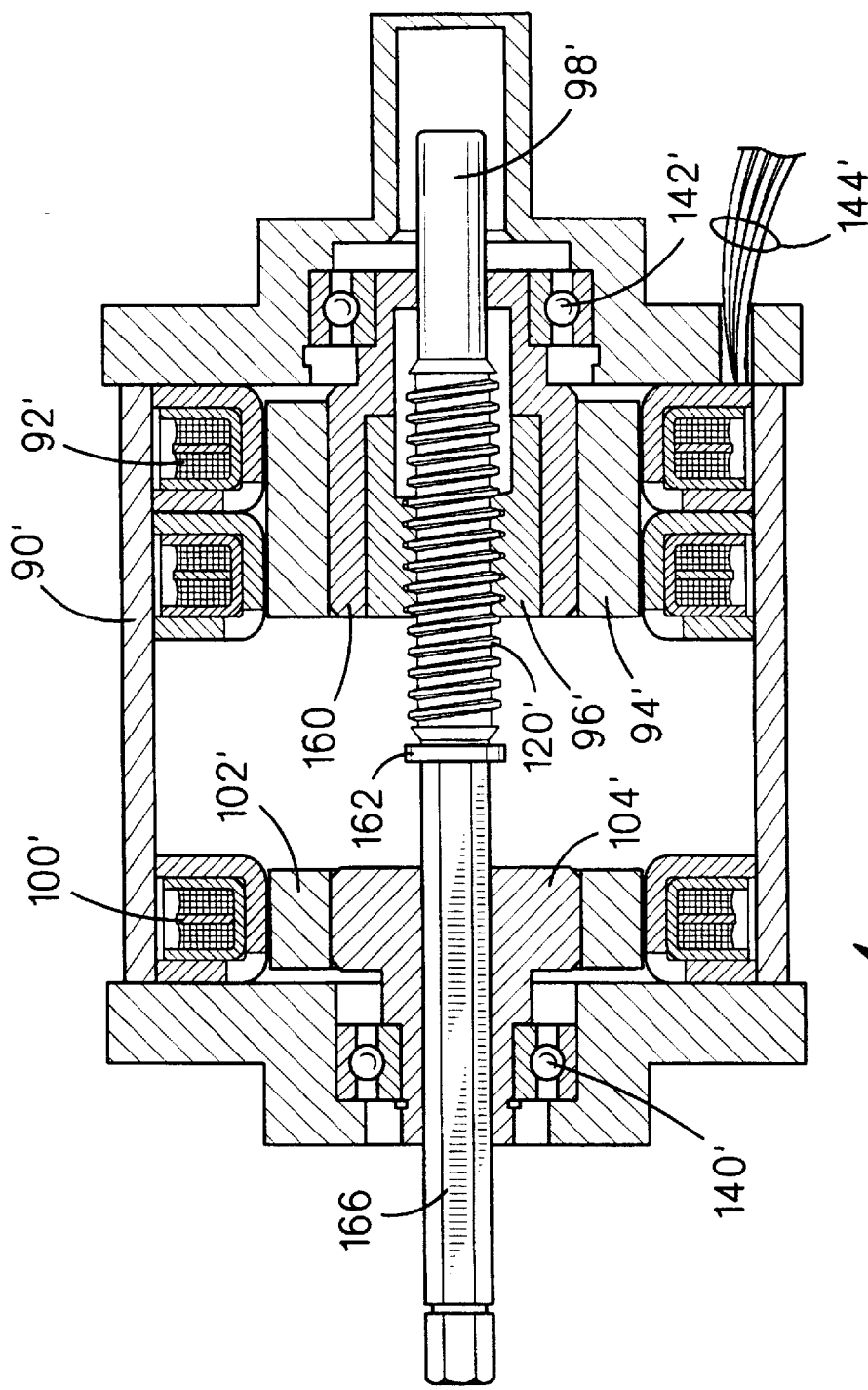
FIG. 4 is a side elevational view, partially in cross-section and partially cut-away, of an electromagnetic device according to a fourth embodiment of the present invention.

FIG. 4 illustrates a linear/rotary electric motor, constructed according to a fourth embodiment of the present invention, the motor being generally indicated by the reference numeral 80'. Since motor 80' is a variation of motor 80 (FIG. 2), common elements thereof are given primed reference numerals and reference should be made to FIG. 2 for a description of the elements and the operation thereof to the extent not described with reference to FIG. 4.

A first difference between motor 80 and motor 80' is that a bushing 160 has been disposed between permanent magnet 94' and threaded bushing 96' to provide centering support for shaft 98' as shown. Second, permanent magnet 130 and Hall cell 132 (FIG. 2) have been eliminated and controls (not shown) are relied upon for determining the timing of the locking and unlocking of brake 100'/102' and the rotating of rotor 94'/160/96'. An fixed annular flange 162 has been provided on shaft 98' to engage bushing 104' at the end of linear movement to prevent further linear movement during rotation of the shaft. Third, pin 116 and slot 118 (FIG. 2) have been eliminated and replaced with a hexagonal shaped portion 166 of shaft 98' to prevent relative rotational motion of the shaft and bushing 104', the latter being provided with a complementary hexagonal shaped channel axially defined therethrough.

All patent applications, patents, and other documents cited herein are incorporated in their entirety by reference hereinto.

In the embodiments of the present invention described above, it will be recognized that individual elements and/or features thereof are not necessarily limited to a particular embodiment but, where applicable, are interchangeable and can be used in any selected embodiment even though such may not be specifically shown.

Terms such as "upper", "lower", "inner", "outer", "inwardly", "outwardly", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

What is claimed is:

1. A linear/rotary electromagnetic device, comprising:
   (a) a housing;
   (b) first and second stators disposed in said housing;
   (c) first and second rotors disposed in said housing and magnetically interacting, respectively, with said first and second stators;
   (d) said first stator and said first rotor comprising a rotary motor;

(e) said second stator and said second rotor comprising an electromagnetic brake;
(f) a shaft extending through a portion of said housing and axially through said first and second rotors, said shaft having a threaded portion extending through a complementarily threaded portion of one of said first and second rotors;

whereby;

(g) when said electromagnetic brake is locked and said rotary motor is rotated in a first direction, said shaft will move axially in a first direction;
(h) when said electromagnetic brake is locked and said rotary motor is rotated in a second direction, said shaft will move axially in a second direction; and
(i) when said electromagnetic brake is released and said rotary motor is rotated, said shaft will rotate with said rotary motor.

2. A linear/rotary motor, as defined in claim 1, wherein: said threaded portion is within said first rotor.

3. A linear/rotary motor, as defined in claim 1, wherein: said threaded portion is within said second rotor.

4. A linear/rotary motor, as defined in claim 1, wherein: a portion of said shaft passing through an unthreaded one of said first and second rotors is attached to said unthreaded one of said first and second rotors by attachment means which permits relative axial movement of said portion of said shaft and said unthreaded one of said first and second rotors but prohibits relative radial movement of said portion of said shaft and said unthreaded one of said first and second rotors.

5. A linear/rotary motor, as defined in claim 4, wherein: said attachment means comprises a pin extending radially through said portion of said shaft and said unthreaded one of said first and second rotors and fixedly attached to said portion of said shaft, with said pin moveable within at an axial slot defined in said unthreaded one of said first and second rotors.

6. A linear/rotary motor, as defined in claim 4, wherein: said attachment means comprises said portion of said shaft having an hexagonal cross section and a channel defined through said unthreaded one of said first and second rotors having a complementarily shaped cross section.

7. A linear/rotary motor, as defined in claim 1, further comprising: a magnetic sensing element fixedly disposed in said housing to sense when said shaft has reached a maximum axial distance of travel and to thereby cause unlocking of said electromagnetic brake.

8. A linear/rotary motor, as defined in claim 7, wherein: said magnetic sensing element is responsive to a magnet fixedly disposed on said shaft approaching said magnetic sensing element.

9. A linear/rotary motor, as defined in claim 7, wherein: said magnetic sensing element is responsive to a magnet disposed on said one of said first and second rotors approaching said magnetic sensing element.

10. A linear/rotary motor, as defined in claim 1, wherein: axial movement of said shaft is terminated by a flange formed on said shaft engaging an element in said linear/rotary motor.

* * * * *